(12) United States Patent
Harding et al.

(10) Patent No.: US 7,344,626 B2
(45) Date of Patent: Mar. 18, 2008

(54) METHOD AND APPARATUS FOR DETECTION OF ABNORMAL TRACES DURING ELECTROCHEMICAL ANALYTE DETECTION

(75) Inventors: Ian Harding, Somerville, MA (US); Richard Williams, Cambridge, MA (US)

(73) Assignee: Agamatrix, Inc., Salem, NH (US)

( * ) Notice: Subject to any disclaimer, the term of this patent is extended or adjusted under 35 U.S.C. 154(b) by 566 days.

(21) Appl. No.: 10/907,818

(22) Filed: Apr. 15, 2005

(65) Prior Publication Data
US 2006/0231425 A1 Oct. 19, 2006

(51) Int. Cl.
*C12M 1/00* (2006.01)
*C12Q 1/54* (2006.01)

(52) U.S. Cl. .......................... 204/403.01; 204/403.02; 204/400; 204/194; 205/777.5

(58) Field of Classification Search ................ 204/401, 204/403.01–403.15
See application file for complete search history.

(56) References Cited

U.S. PATENT DOCUMENTS

| | | | |
|---|---|---|---|
| 5,243,516 A | 9/1993 | White | |
| 5,266,179 A | 11/1993 | Nankai et al. | |
| 5,320,732 A | 6/1994 | Nankai et al. | |
| 5,352,351 A | 10/1994 | White et al. | |
| 5,438,271 A | 8/1995 | White et al. | |
| 5,942,102 A | 8/1999 | Hodges et al. | |
| 6,153,069 A | 11/2000 | Pottgen et al. | |
| 6,284,125 B1 | 9/2001 | Hodges et al. | |
| 6,428,684 B1* | 8/2002 | Warburton | 205/775 |
| 6,616,819 B1 | 9/2003 | Liamos et al. | |
| 2002/0084196 A1* | 7/2002 | Liamos et al. | 205/792 |
| 2003/0106809 A1 | 6/2003 | Kermani et al. | |
| 2003/0178322 A1 | 9/2003 | Iyengar et al. | |
| 2005/0067301 A1 | 3/2005 | Morita et al. | |
| 2005/0069892 A1 | 3/2005 | Iyengar et al. | |
| 2005/0258034 A1 | 11/2005 | Iketaki et al. | |

FOREIGN PATENT DOCUMENTS

| | | |
|---|---|---|
| EP | 1081490 | 3/2001 |
| WO | 03/040728 | 5/2003 |
| WO | WO 03/060154 A2 | 7/2003 |
| WO | WO 03/069304 A2 | 8/2003 |
| WO | WO 2005/022143 | 8/2004 |

* cited by examiner

*Primary Examiner*—Barbara L. Gilliam
*Assistant Examiner*—Bach Dinh
(74) *Attorney, Agent, or Firm*—Marina Larson & Associates, LLC (57) ABSTRACT

Detection of abnormal signal traces in electrochemical measurements generated using an electrochemical test strip to which a potential is applied allows for an indication of an erroneous analyte determination. The current trace has an expected shape in which a peak current is observed a time $t_{peak}$ after which there is a decrease in current. To detect abnormal signal traces, the time $t_{peak}$ is determined experimentally and compared with an expected value, $t'_{peak}$, and if the difference between the two values to over a predetermined threshold, an error message is provided to the user instead of a test result. The value of $t'_{peak}$ is determined as a function of a mobility term that is determined during a potentiometry phase following the amperometric measurements.

12 Claims, 9 Drawing Sheets

METHOD AND APPARATUS FOR DETECTION OF ABNORMAL TRACES DURING ELECTROCHEMICAL ANALYTE DETECTION

BACKGROUND OF THE INVENTION

This application relates to identification of abnormal traces during electrochemical determination of analytes such as glucose, and to a meter, and meter-test strip combination for use in such a method.

Small disposable electrochemical test strips are frequently used in the monitoring of blood glucose by diabetics. Such test strips can also be employed in the detection of other physiological chemicals of interest and substances of abuse. In general, the test strip comprises at least two electrodes and appropriate reagents for the test to be performed, and is manufactured as a single use, disposable element. The test strip is combined with a sample such as blood, saliva or urine before or after insertion in a reusable meter, which contains the mechanisms for detecting and processing an electrochemical signal from the test strip into an indication of the presence/absence or quantity of the analyte determined by the test strip.

Figure 1:
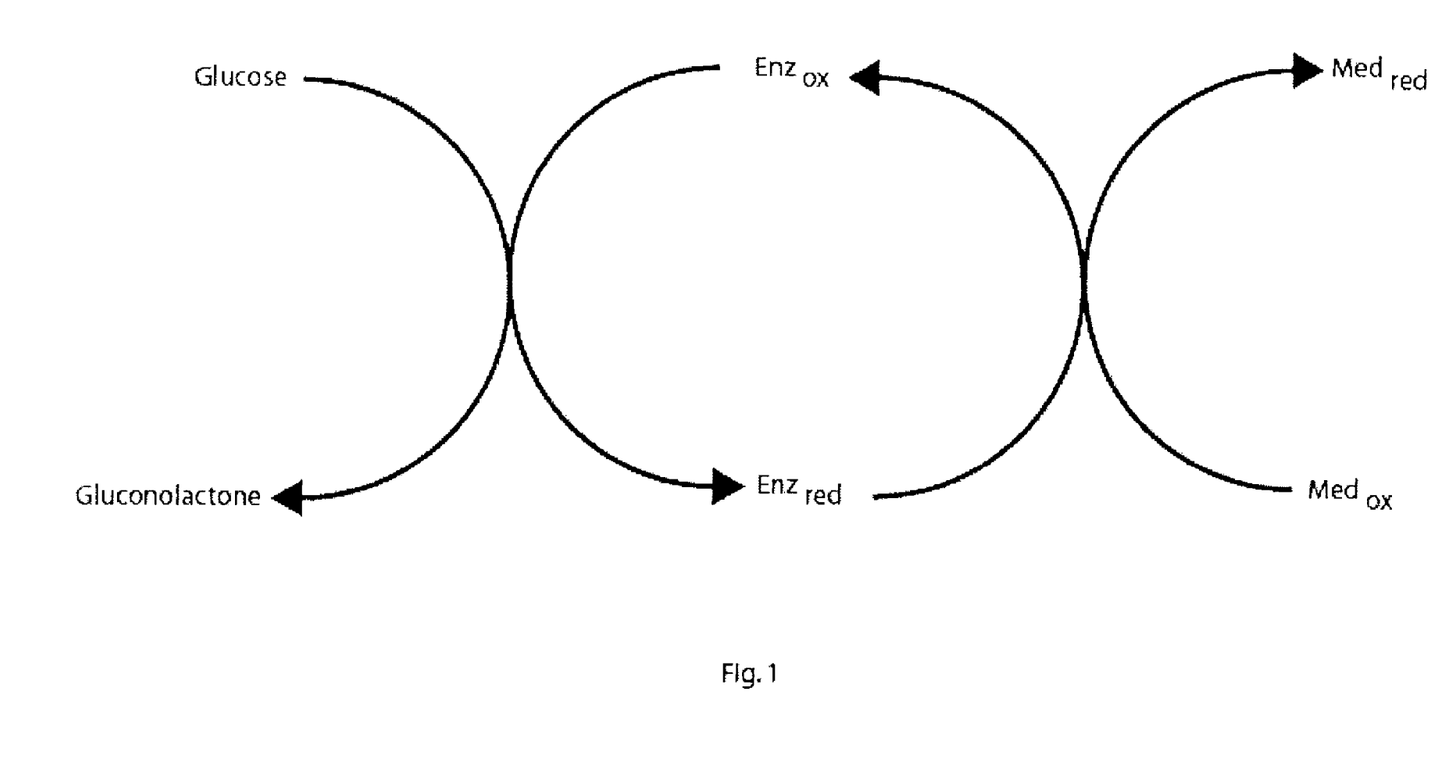
FIG. 1 shows the electron transfer reactions that occur in a conventional amperometric glucose detector.

Electrochemical detection of glucose is conventionally achieved by applying a potential to an electrochemical cell containing a sample to be evaluated for the presence/amount of glucose, an enzyme that oxidizes glucose, such as glucose oxidase, and a redox mediator. As shown in FIG. 1, the enzyme oxidizes glucose to form gluconolactone and a reduced form of the enzyme. Oxidized mediator reacts with the reduced enzyme to regenerate the active oxidase and produced a reduced mediator. Reduced mediator is oxidized at one of the electrodes, and then diffuses back to either be reduced at the other electrode or by the reduced enzyme to complete the cycle, and to result in a measurable current. The measured current is related to the amount of glucose in the sample, and various techniques are known for determining glucose concentrations in such a system are known. (See for example, U.S. Pat. Nos. 6,284,125; 5,942,102; 5,352,351; and 5,243,516, which are incorporated herein by reference.)

In meters that analyze electrochemical signals, assumptions are made about the characteristics of the signal in order to minimize the processing capability that is required in the meter, and processing time that is required. Not all traces, however, will meet these ideal characteristics. For example, when a user contacts the test strip twice in a short period of time, uses an inappropriate sample, flicks the end of the test strip, the signal characteristics may be abnormal. Other sources of signal abnormality may include use of a wet or damp test strip, or a test strip in which parts of the reagent have come loose from the surface of the working electrode. Abnormal signals of this type can still produce a result, but because the data processing assumes signal characteristics that are not in fact present, the result is unreliable. It would therefore be desirable to have a method for identifying abnormal traces that did not require significant processing or add additional component requirements to the meter or test strips.

SUMMARY OF THE INVENTION

The present invention provides a method for detecting abnormal traces in an electrochemical determination of an analyte in a sample comprising the steps of:

(a) introducing the sample to an electrochemical test strip having working and counter electrodes;

(b) applying a potential difference, $V_{app}$, between the electrodes of the test strip and observing a current signal sufficient to provide a determination of analyte in the sample;

(c) determining a time $t_{peak}$, said time occurring at a maximum in the current at the point of changeover when sufficient material is available at the counter electrode to balance the consumption of analyte at the working electrode;

(d) switching off the applied potential at time $t_{switch}$, (e) determining a time, $t_{mob}$, wherein $t_{mob}$ is the time after the applied potential is switched off, that it takes for the potential between the electrodes to decay to a pre-determined value, (f) calculating an expected value of $t_{peak}$, $t'_{peak}$, where $t'_{peak}$ is a function of $t_{mob}$, and (g) comparing the absolute value of $t_{peak} - t'_{peak}$ to a predetermined threshold value, rejecting the test if the absolute value of $t_{peak} - t'_{peak}$ is greater than the threshold value.

DETAILED DESCRIPTION OF THE INVENTION

I. Definitions

As used in the specification and claims of this application, the following definitions should be applied:

(a) "analyte" refers to a material of interest that may be present in a sample. In the present application, the examples use glucose as an analyte, but the present invention is independent of both the type and amount of analyte. Accordingly, application to glucose detection systems should be viewed as merely a specific and non-limiting embodiment.

(b) "Cottrell decay" or "Cottrell current" is current that can be modeled by the Cottrell equation, i.e., $$1/I^2 \propto t$$

where I is the current and t is time. The square root of the slope of $1/I^2$ versus t is a parameter called the "Cottrell slope."

(c) "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present.

(d) "electrochemical test strip" refers to a strip having at least two electrodes, and any necessary reagents for determination of an analyte in a sample placed between the electrodes. In preferred embodiments, the electrochemical test strip is disposable after a single use, and has connectors for attachment to a separate and reusable meter that contains the electronics for applying potential, analyzing signals and displaying a result.

(e) "facing electrodes" are a pair of electrodes disposed parallel to but in a separate plane from each other. Some or all of the opposed surfaces of a pair of facing electrodes overlap, such that potential gradients and current flows between the electrodes are in a direction substantially perpendicular to the opposed surfaces. Facing electrodes are distinguished from side-by-side electrodes in which the two electrode surfaces lie in the same plane, and in which potential gradients and current flow is substantially parallel to the surface of the electrodes. The present invention can be used with either facing or side-by-side electrodes.

(f) "mediator" refers to a chemical species that is electrochemically detected. Numerous electron transfer mediators suitable for detection of analytes such as glucose are known, and include without limitation iron, ruthenium, and osmium compounds. In some embodiments of the invention, the mediator is produced through one or more reaction steps and is related to the concentration of the actual analyte, such as glucose. The present invention is also applicable, however, to circumstances in which the detected chemical species is the reduced form of the analyte to be detected, and this is also an embodiment of the invention.

(g) "mobility" refers to the mobility of the mediator in the electrochemical test cell. Mediator mobility is a property of the mediator itself, i.e., the diffusion coefficient, but is also dependent on other sample properties such as hematocrit and viscosity.

(g) "oxygen carrying capacity" refers to the capacity of the sample to hold oxygen, in dissolved form and in a red blood cell reservoir.

(h) "predetermined" is used in this application to refer to amounts or values that are determined empirically for a particular meter or test strip or meter/strip combination. The predetermined amounts or values will reflect an optimization for the needs of the user, taking into account the confidence levels needed, and need not achieve the best possible results or 100% accuracy.

(i) "switching off" of the applied potential refers to the creation of an open circuit that forces the current to be zero (by opening a switch or introducing a high impedance into the circuit) that allows a built-up chemical concentration gradient and ion adsorption in the double layer to determine the potential between the electrodes. This is not the same thing as setting the voltage to zero volts.

(j) "$t_{mob}$" is a time determined experimentally during an analysis that reflects the mobility of mediator in a particular sample in a particular test cell. $t_{mob}$ is the time after the applied potential is switched off, that it takes for the potential between the electrodes to decay to a pre-determined value.

(k) "$t_{peak}$" is the time at which maximum current occurs during the course of the measurement cycle of the sample being processed in the individual test strip, exclusive of any initial current spike associated with double-layer charging.

This peak current occurs at the point of changeover when sufficient material is available at the counter electrode to balance the consumption of analyte at the working electrode. At this point, the consumption of analyte at the working electrode becomes limiting. This rapid fall in current that results from the diffusion-limited consumption of analyte is what gives rise to the characteristic Cottrell decay.

(l) a "trace" is the shape of a signal versus time, whether the signal is current or voltage.

Numerical values in the specification and claims of this application should be understood to include numerical values which are the same when reduced to the same number of significant figures and numerical values which differ from the stated value by less than the experimental error of the technique used to measure the value.

II. Determination of Analyte such as Glucose

Figure 2:
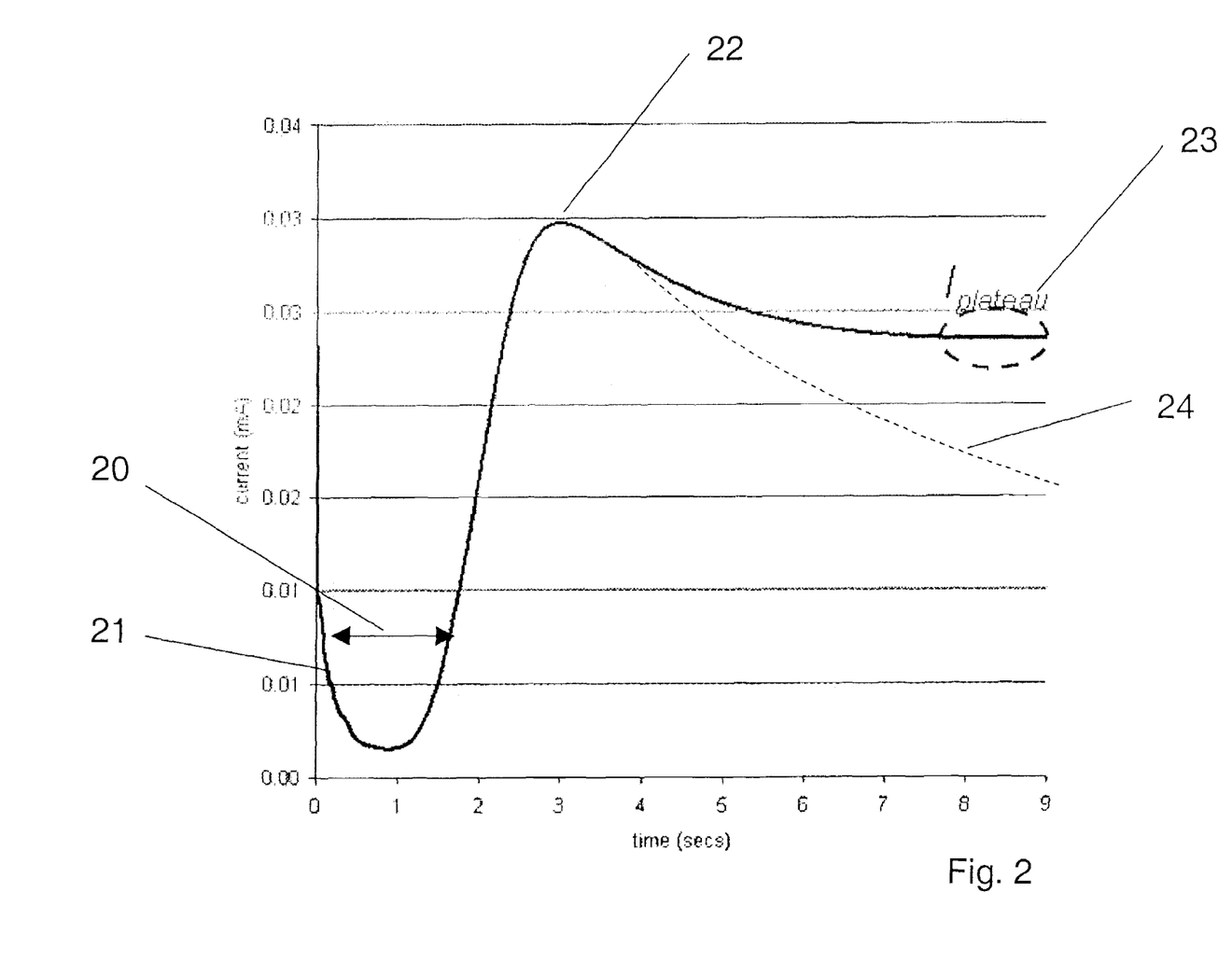
FIG. 2 show the type of current versus time profiles observed in two different electrochemical test strip configurations.

FIG. 2 shows current versus time profiles observed in two different electrochemical test strip configurations, one with facing electrodes and one with side-by-side electrodes, where the electrochemical reagents are initially disposed only on the working electrode, and not on the counter electrode. In both cases, the current trace shows an immediate initial current 21 on the time scale shown following application of the potential. This current is associated with the initial charging of the double layer at the surface of the electrodes. Thereafter, the current decreases, because current is dependent on the mediator diffusing from the working electrode (where the reagent comprising the mediator was deposited during manufacture) to the counter electrode. The duration of this reduced current (indicated by arrow 20) is dependent on the distance between the electrodes, and on the mobility of the mediator. Mediator mobility is a property of the mediator itself, i.e., the diffusion coefficient, but is also dependent on other sample properties such as hematocrit and viscosity. After the period of reduced current 20, the current rapidly rises to a peak current 22. In the case of facing electrodes, the current declines to a plateau current 23 which reflects the recycling or shuttling of mediator between the electrodes. In the case of side-by-side electrodes, the current continues to decay in the time scale indicated, as indicated by dashed line 24. At longer times, this curve 24 may also shows effects of recycling/shuttling of mediator if the electrodes are placed close enough together.

In the region of the decay following the peak, before recycling becomes dominant, the current decay can be modeled by the Cottrell equation, i.e., $$1/I^2 \propto t$$

where I is the current and t is time. Cottrell analysis can be utilized to determine glucose concentration as described in U.S. Pat. Nos. 5,243,516; 5,352,351 and 6,284,125. Commonly assigned U.S. patent application Ser. No. 10/907,803, filed Apr. 15, 2005, which is incorporated herein by reference, discloses a Cottrell analysis of analyte concentration that includes a mobility correction obtained when the applied potential is switched off after monitoring the current to obtain data for determination of analyte.

As an alternative to Cottrell analysis, current in the plateau region 23 of FIG. 2 can be used to determine analyte concentration. This type of measurement is particularly applicable when using conduction cell test strips, as described in commonly assigned U.S. patent application Ser. No. 10/924,510, which is incorporated herein by reference.

In determining the numerical value of analyte concentration which is communicated/displayed to a user, one or more correction factors based on calibration values for a lot of strips, or measurements made during the analysis may be applied. Further, it will be understood that a look up table or other conversion system may be used to convert a raw value into a meaningful value for communication/display to the user.

III. Abnormal Trace Determination

The present invention provides a method for the detection of abnormal signal traces in electrochemical measurements generated using an electrochemical test strip to which a potential is applied. The current trace has an expected shape such as that in FIG. 2 in which a peak current, $i_{peak}$ is observed at time $t_{peak}$ after which there is a decrease in current. In accordance with the invention, time $t_{peak}$ is determined experimentally and compared with an expected value, $t'_{peak}$, and if the difference between the two values is over a predetermined threshold, an error message is provided to the user instead of a test result.

The value $t'_{peak}$ is determined as a function of measurements taken during a subsequent operation in potentiometric mode that occurs when the applied potential is switched off after current measurements sufficient to make a determination of analyte have been made. During this potentiometric mode, a time value $t_{mob}$ is determined. $t_{mob}$ is an indicator of the mobility of charge carrier within the sample, and thus is affected by the same factors that affect the time at which peak current is observed.

Once $t_{peak}$ and $t'_{peak}$ are determined, the difference between the values is determined. If the absolute value of this difference is greater than a predetermined threshold value, an abnormal trace is assumed and an error message is presented in place of a result.

Evaluating an analysis for abnormal traces in this way is particularly effective since $t_{peak}$ and $t_{mob}$ are determined with minimal hardware or processing requirements, and since each can be used independently in improving the accuracy or efficiency of analyte determination. For example, commonly assigned U.S. patent application Ser. No. 10/907,815, which is incorporated herein by reference, discusses the use of $t_{peak}$ in a method for determining analyte concentrations, for example glucose concentrations, that utilizes a dynamic determination of the appropriate time for making a glucose measurement, for example when a current versus time curve substantially conforms to a Cottrell decay, or when the current is established in a plateau region. This allows each strip to operate in the shortest appropriate time frame, thereby avoiding using an average measurement time that may be longer than necessary for some strips and too short for others. Commonly assigned U.S. patent application Ser. No. 10/907,803, filed Apr. 15, 2005, describes the use of $t_{mob}$ in the determination of an additive correction factor to correct a measured analyte concentration for the effects of oxygen carrying capacity of the sample, including hematocrit.

III. Determination of $t_{peak}$

In accordance with the invention, a sample in a electrochemical test strip is processed to generate a current profile as shown in either line in FIG. 2. Thus, in a first step, a diffusion-limiting voltage is applied to a test strip rapidly after a sample is introduced to the chamber. The polarity of the electrodes is such that a first electrochemically detectable species whose concentration depends on the analyte will be consumed at the electrode the reagent is deposited on (the 'working electrode'), and balanced by a counter reaction of a second species in excess in the reagent at the opposite electrode (the 'counter electrode'). In this way, a signal limited by consumption of the first species will not occur until there is excess of the second species at the opposite electrode, a condition that is limited by mobility. The voltage applied to the test strip to stimulate a current through the sample should be sufficiently high to ensure the current reaches a limit set by the mobility of species, the so-called "diffusion limited current." Further, this voltage needs to have been applied sufficiently early that the change from current limited by arrival of species at the counter electrode to current limited by arrival of analyte-dependant species at the working electrode can be observed under diffusion-limited conditions.

The initial current surge associated with application of the potential (due to establishing electrode double layers and consuming surface impurities) must have had sufficient time to die away to leave a baseline current that represents arrival of species at the counter electrode. This baseline is monitored and will start to increase rapidly when significant amounts of species become available to support reaction at the counter electrode. The rapid increase is monitored and a point of changeover noted. This changeover occurs when sufficient species are available to support reaction at the counter electrode to balance consumption of analyte-related species at the working electrode, which then becomes limiting. The time to this changeover is thus an indicator of mobility, and is designated in this application as $t_{peak}$. The change in limiting species results in the rapid consumption of analyte-related species near the working electrode and a rapid fall in the current as a result.

Identification of the peak is done by inspecting amperometric data as it is produced for a local maximum. Such inspection is best not started too early since filling, patient contact with the sample and initial current surges should be ignored: starting inspection from a time point of 1 to 2 seconds, for example 1.5 seconds after sample detection is adequate for most sub microliter electrochemical test strips. In one embodiment for the invention, the local maximum is the highest current in a time window from the present stretching back a set period: two seconds is good because it fits well with the time that must elapse for establishing a stable diffusion profile. When the local maximum is at the earliest point of the time window and has not been replaced by a higher maximum in later data, the peak can be assumed to have been identified as this local maximum. Identification can be improved further by applying digital or analogue filters to remove the effects of sharp spikes in the data that are not representative of diffusional processes. Other techniques, such as curve fitting to identify peaks of a particular expected form may also be used, or the amperometric signal can be evaluated to determine the time when the first derivative is zero.

In order to obtain a value for $t_{peak}$ which is an accurate measure of the time from the introduction of the sample, a mechanism for defining the start of the measurement cycle is required. As is apparent from looking at FIG. 2, the numerical value of $t_{peak}$ is dependent on the point in time which is assigned a zero value. If blood is applied to a test strip and a period of time is allowed to pass prior to starting the test cycle, enzyme and mediator will dissolve and tend to diffuse across evenly in the space between the electrodes. This will result in the shortening, if not the elimination of the interval 20. Thus, in practicing the method of the invention, it is important to have a consistent start time relative to sample application that is before diffusion to eliminate interval 20 can occur. In practice, this result can be obtained by automatically starting the cycle upon, or within a fixed period of time after the addition of sample to an electrochemical test strip that is already disposed in the meter.

Mechanisms for automatically starting the measurement cycle include, without limitation, (1) measuring a current or a resistance between the working and counter electrodes in the electrochemical test strip; and (2) measuring a current or a resistance between two electrodes wherein at least one of the two electrodes is not the working electrode or the counter electrode. Thus, the current or resistance could be measured between a combination of a third electrode and either the working or counter electrode, or between a third and fourth electrode. It will be appreciated that the current measured in this case can be a current in response to a low voltage, insufficient to produce redox chemistry indicative of analyte, although this requires a sample that has ionic charge carriers such as Na+ and Cl− either inherently present or added.

Sample detection to initiate timing of an assay may also be done passively as described in US Patent Publication US2003/0106809, which is incorporated herein by reference.

In one embodiment of the invention, while the meter is waiting for sample to be introduced after having been turned on by the user or by detection of a sample strip, it is pulsing the voltage, Vw, of the working electrode while holding the voltage, Vc, of the counter electrode constant. This pulsed voltage can conveniently be shaped almost as a sine wave using a low pass filter on Vw. The frequency of pulsing is dependent on the hardware chosen, and is suitably in the range of 20 to 50 Hz, for example 33 or 40 Hz.

When sample is introduced, the current traveling through the electrodes should spike with each pulse. To make a more reliable determination that sample has been introduced, however, in one embodiment of the invention, a plurality of consecutive spikes are required to count as an indication of sample application. For example, a positive indication of sample application may require a current spike in response to 3 of 4, 4 of 5, 4 of 6, or 6 of 8 consecutive voltage pulses.

Calculation of the starting time is based on an assumed sample application time prior to the triggering time. For example, in the case that 3 of 4 current spikes are required, it is assumed that sample was introduced 3 voltage pulses before the trigger. Therefore, the trigger happens at: t=(3/pulse frequency). In the case that 6 of 8 current spikes are required, it is assumed that sample was introduced 6 voltage pulses before the trigger. Therefore, the trigger happens at: t=(6/pulse frequency). The value of $t_{peak}$ is determined with reference to this starting time.

IV. Determination of $t_{mob}$

Figure 3:
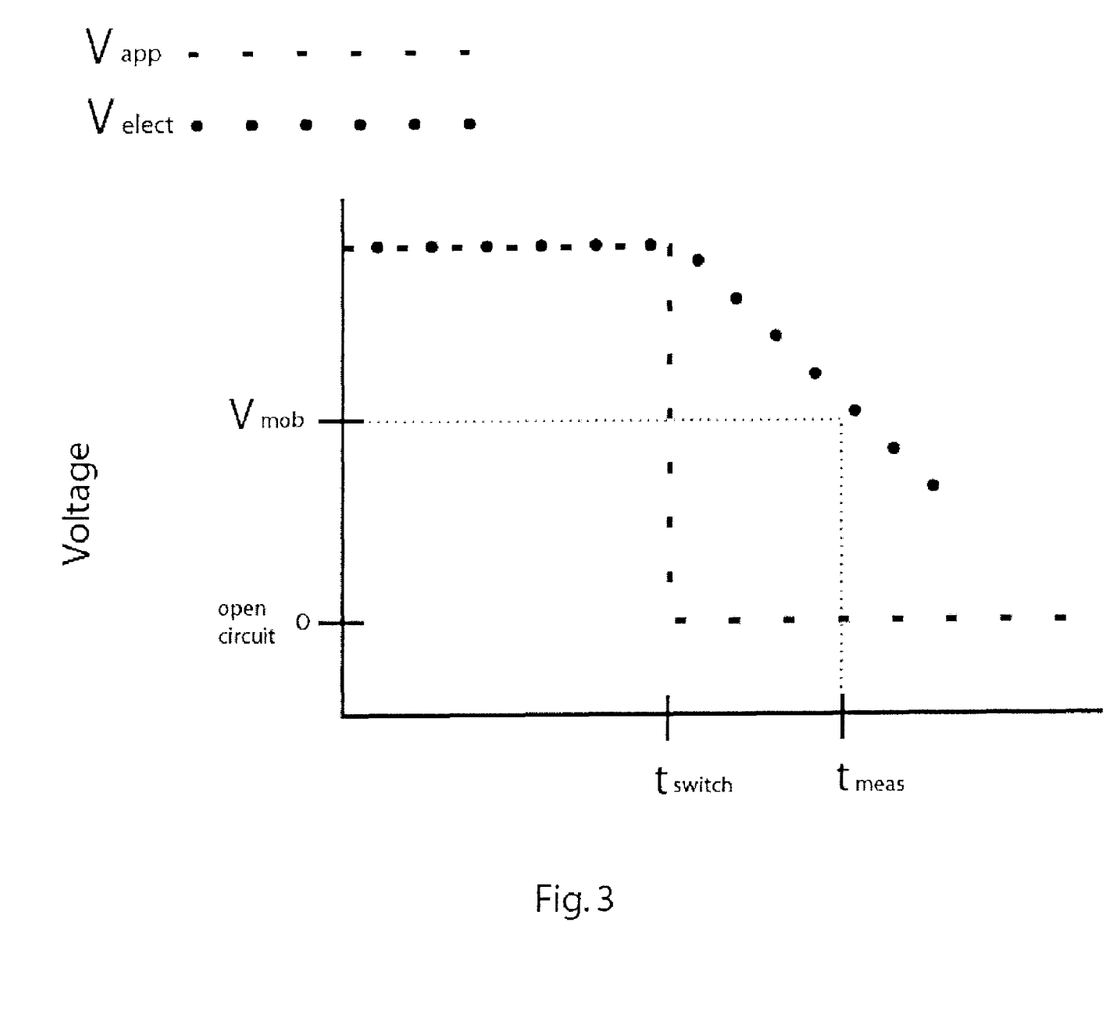
FIG. 3 shows a plot of voltage versus time, when applied voltage is switched off.

After measurements sufficient to allow determination of a raw analyte concentration, the applied potential is switched off at a time $t_{switch}$. At this point, a chemical potential gradient exists between the electrodes as a result of the unequal distribution of oxidized and reduced mediator. This chemical potential gradient decays over time after the potential is switched off, and the rate of this decay is dependent on the mobility of the mediator in the sample. (See commonly assigned U.S. patent application Ser. No. 10/924,510, which is incorporated herein by reference.) FIG. 3 shows the applied potential, $V_{app}$, and the measured potential at the electrodes, $V_{elect}$, as a function of time (in arbitrary units), commencing at a time after the current measurement that is used in the apparatus to determine raw analyte concentration. Note that the conversion of measured current to a measurement of raw analyte concentration need not be done prior to the switching off of the potential.

In accordance with one embodiment of the present invention, the decay in potential is monitored until the observed potential has decreased to a pre-determined value, $V_{mob}$. Decreases to around 50 mV are convenient where the applied voltage is on the order of 300 mV, although somewhat smaller values such as 47 mV or 48 mV may be found to provide optimum results in particular experimental configurations. In general, $V_{mob}$ is suitably 0.025 to 0.1V For example, in glucose determinations with a $V_{app}$ of 250 to 300 mV, $V_{mob}$ is suitably in the range of 25 to 100 mV, preferably 45 to 50 mV.

The time at which this drop has occurred is noted on FIG. 3 as $t_{meas}$ and $t_{mob}$ is given by:

$$t_{mob}=t_{meas}-t_{switch}.$$

Other ways of determining a measure of the rate of decay may also be employed. For example, an instantaneous slope of the decay of the potential can be determined, or the decrease in voltage over a predetermined time can be used. The meter may also select a particular time window and perform a linear regression on V versus log(t) or ln(t) to find $t_{mob}$ which is the time to a particular voltage. If the $V_{mob}$ does not fall within the selected window, a projection based on this linear fit can be used. The specific methodology is not critical, provided that the value of the measured decay is taken into account in determining the correction function.

V. Determination of $t'_{peak}$

The expected value of $t_{peak}$ is determined as a function of the determined value of $t_{mob}$. In accordance with a first embodiment of the invention:

$$t'_{peak}=a_1(t_{mob})+a_2$$

The constants $a_1$ and $a_2$ in this case are empirically determined by assuming a linear relationship with slope $k_1$ and intercept $k_2$ between $t_{peak}$ and $t_{mob}$.

Because $t_{peak}$ is a function of analyte concentration and $t_{mob}$ is not, a more robust approach takes determined analyte concentration into account in determining $t'_{peak}$. Thus, additional terms and constants can appropriately be determined using calibration reactions over a range of analyte concentrations and sample mobilities, for example hematocrit, likely to be encountered and to include terms or factors indicative of the measured analyte amount in the calculation of $t'_{peak}$. Based on such an analysis, suitable equations may have forms such $$t'_{peak}=k_1 \times t_{mob}^n+k_2(\text{CottrellSlope}^m)+k_3$$

or $$t'_{peak}=[k_1 \times t_{mob} \times \text{CottrellSlope}^m]+[k_2 \times t_{mob}^n]+[k_3 \times t_{mob}^n \times \text{CottrellSlope}^m]+k_4$$

where $k_1$-$k_4$ are empirically determined constants, and the CottrellSlope is the square root of the slope of $1/I^2$ versus t in the Cottrell decay region of the current curve, and n and m are experimental positive or negative integer or fractional numbers, for example ½, ⅓, ¾, −½, −⅓, or −¼. In one specific combination, n is ½ and m is −1.

Figure 4A:
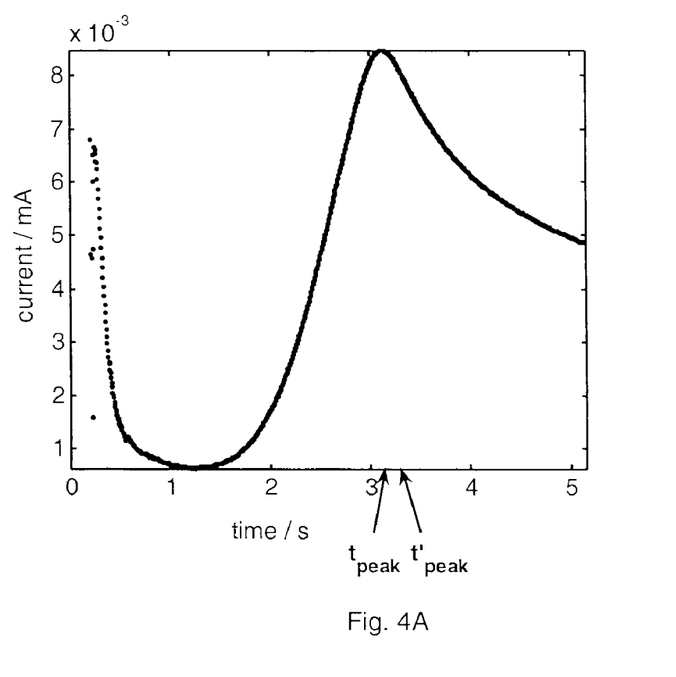
FIGS. 4A and 4B show a normal trace in which $t_{peak}$ and $t'_{peak}$ as determined are substantially the same and an abnormal trace in which $t_{peak}$ and $t'_{peak}$ as determined are different.
Figure 4B:
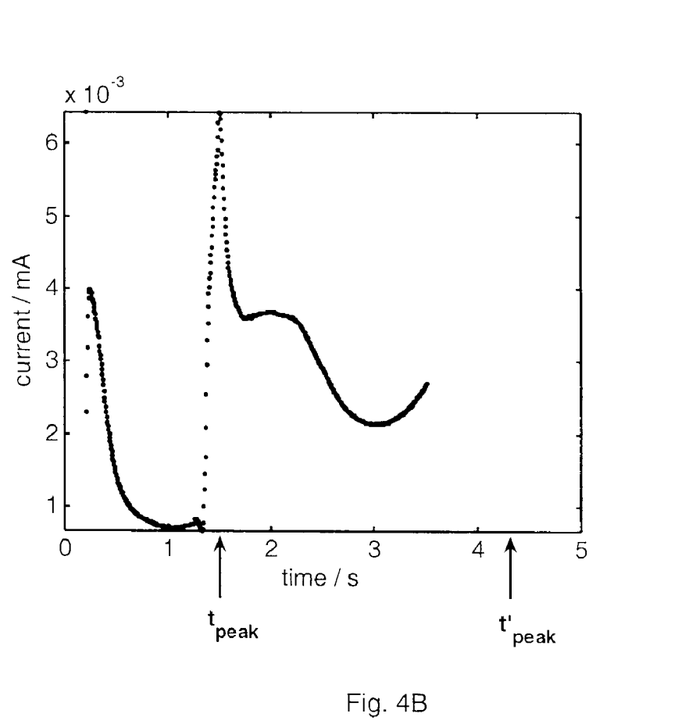

FIG. 4A shows a normal trace in which $t_{peak}$ and $t'_{peak}$ as determined are substantially the same. FIG. 4B shows an abnormal trace in which $t_{peak}$ and $t'_{peak}$ as determined are different.

VI. Meter of the Invention

The method of the invention can be used with any strip that has a working and a counter electrodes, with the proviso that only one electrode (the working electrode) has reagent on it at the start process, providing that a meter apparatus is provided that can receive the strip and provide the necessary applications of voltage and signal processing. Such a meter also forms an aspect of the present invention. Thus, the invention provides a meter for receiving an electrochemical test strip having working and counter electrodes and providing a determination of an analyte in a sample applied to the electrochemical test strip when received in the meter, said meter comprising (a) a housing having a slot for receiving an electrochemical test strip;

(b) communications means for receiving input from and communicating a result to a user; and (c) means for applying a potential and to determine analyte concentration from an observed current, (d) means determining a time $t_{peak}$, said time occurring at a maximum in the current at the point of changeover when sufficient material is available at the counter electrode to balance the consumption of analyte at the working electrode;

(e) means for switching off the applied potential at time $t_{switch}$, and determining a time, $t_{mob}$, wherein $t_{mob}$ is the time after the applied potential is switched off, that it takes for the potential between the electrodes to decay to a pre-determined value, (f) means for calculating an expected value of $t_{peak}$, $t'_{peak}$, where $t'_{peak}$ is a function of $t_{mob}$, comparing the absolute value of $t_{peak}-t'_{peak}$ to a predetermined threshold value, and generating an error message if the absolute value of $t_{peak}-t'_{peak}$ is greater than the threshold value.

Figure 5:
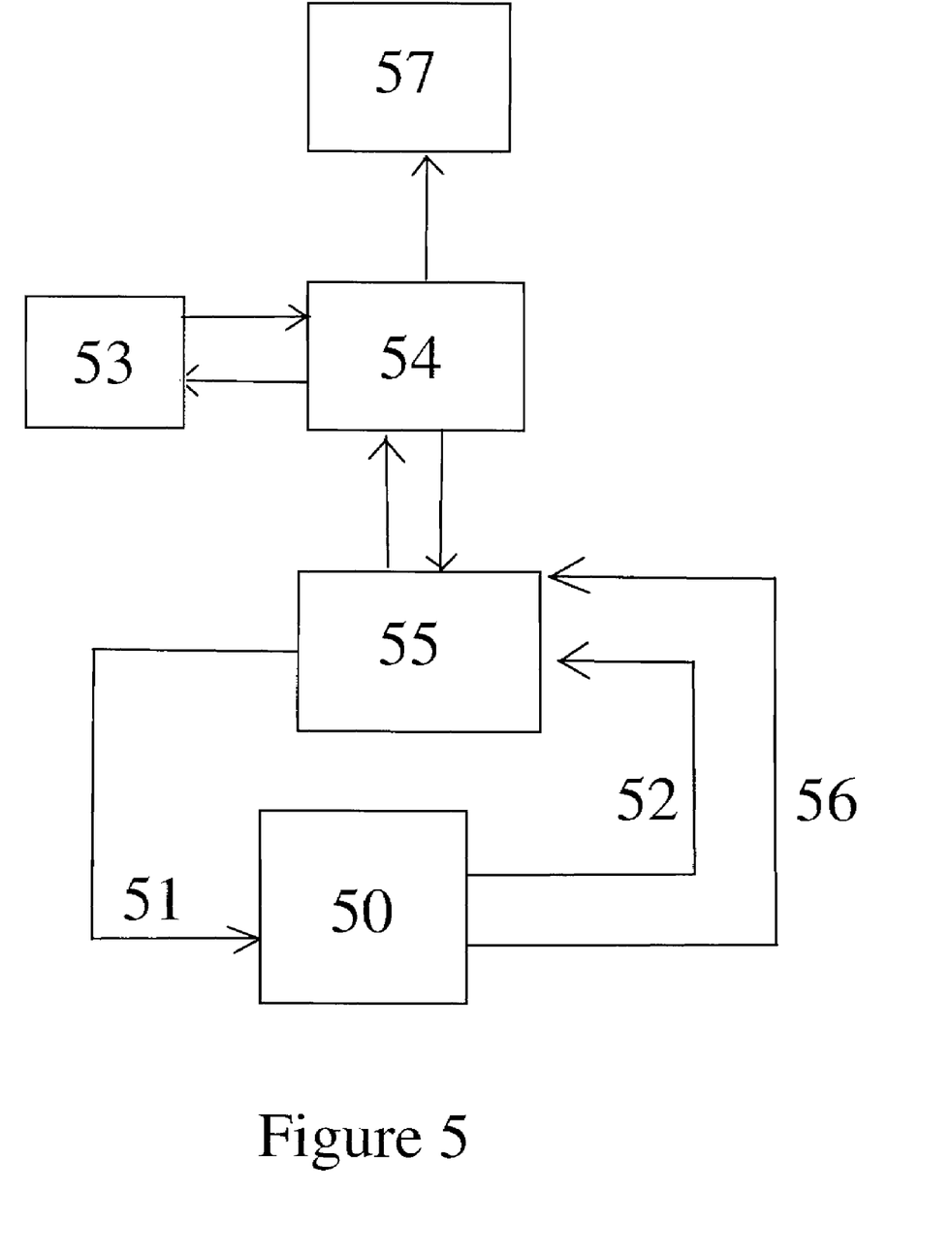
FIG. 5 illustrates the components of an embodiment of the invention schematically.

FIG. 5 illustrates the components of an embodiment of the invention schematically. As shown in FIG. 5, potential 51 is generated by circuit 55 and applied to a test strip 50. This results in a current signal 52 which is passed stored at 53. At time $t_{switch}$, microprocessor 54 causes circuit 55 to stop applying potential and to start monitoring the potential difference 56 in the test strip, and determine series electrode resistance. $t_{peak}$ is determined from analysis of the current signal 52. $t_{mob}$ is determined from analysis of the potential signal 56 and is used to determine $t'_{peak}$. If the absolute value of the difference between $t_{peak}$ and $t'_{peak}$ is greater than the threshold value retrieved by the processor 54 from the storage 53, an error message is sent to display 57. Otherwise, the stored current data is retrieved from 53 and a result is determined and sent to display 57.

Figure 6:
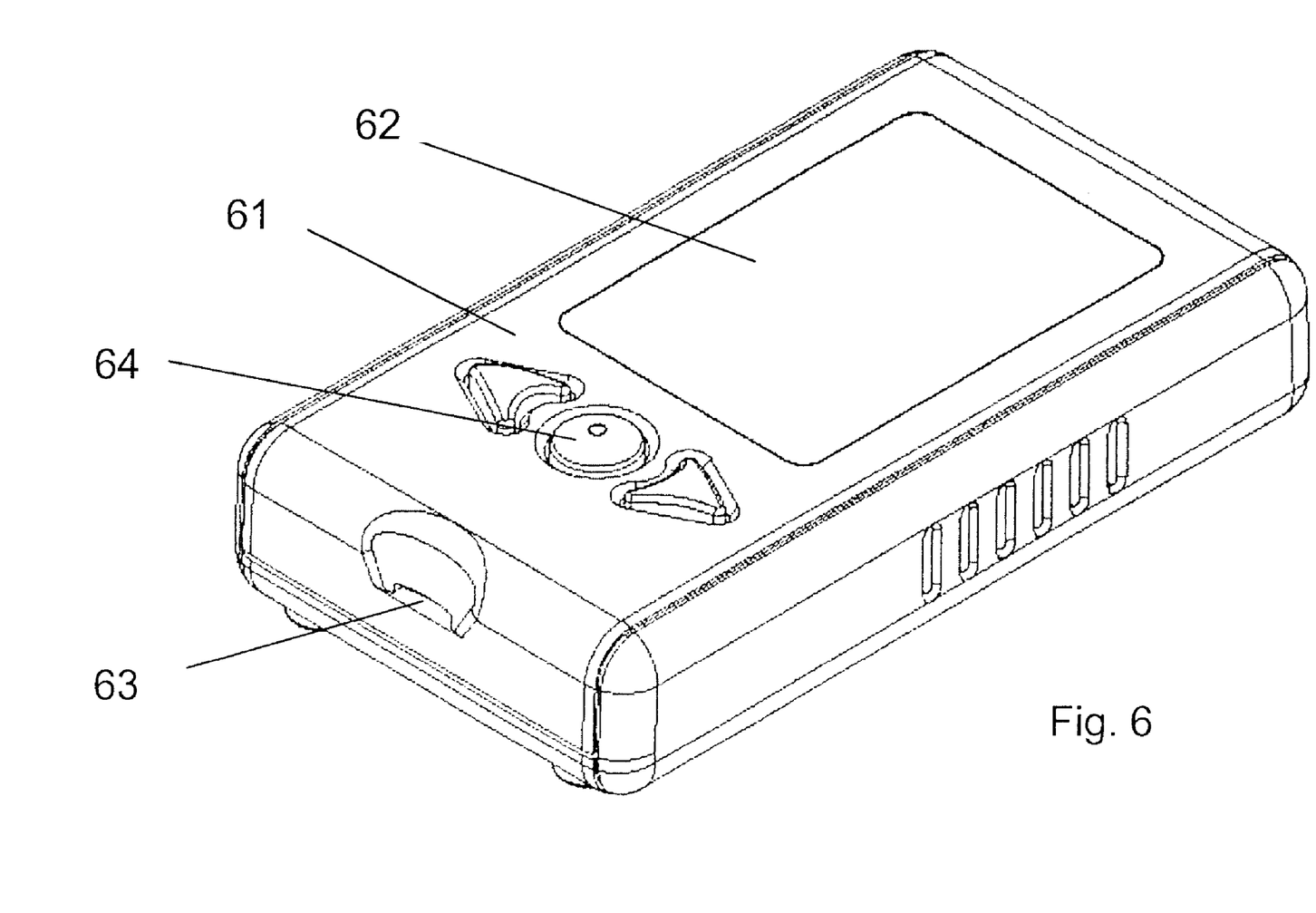
FIG. 6 shows an exterior view of a meter.

FIG. 6 shows an external view of a meter in accordance with the invention. The meter has a housing 61, and a display 62. The housing 61 has a slot 63, into which a test strip is inserted for use. The meter may also have a button 64 for signaling the start of the measurement cycle, or may have an internal mechanism for detecting the insertion of a test strip or the application of a sample. Such mechanisms are known in the art, for example from U.S. Pat. Nos. 5,266,179; 5,320,732; 5,438,271 and 6,616,819, which are incorporated herein by reference. In the meter of the invention, buttons, displays such as LCD displays, RF, infrared or other wireless transmitters, wire connectors such as USB, parallel or serial connections constitute means for receiving input from and communicating a result to a user, and can be used individually and in various combinations.

Figure 7:
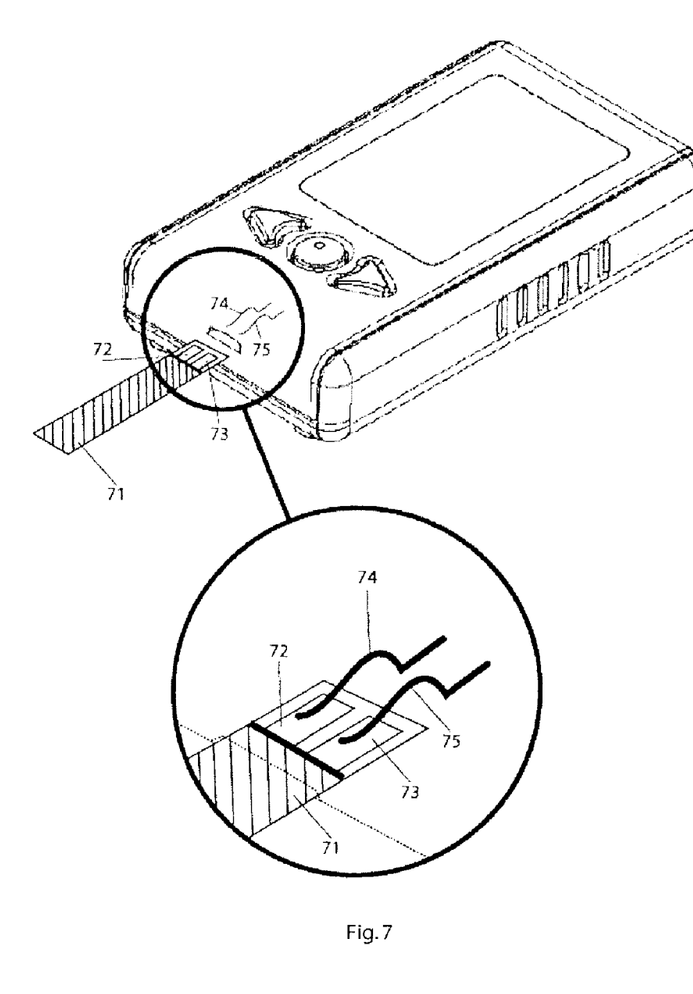
FIG. 7 shows connection of a test strip and connectors in a meter.

FIG. 7 shows an interior view in which the connection of the meter to a test strip is shown. As shown, the test strip 71 has contacts 72, 73 by which the electrodes are placed in electrical contact with contacts 74, 75 of the meter.

The means for means for applying a potential and to determine analyte concentration from an observed current, means determining a time $t_{peak}$, said time occurring at a maximum in the current at the point of changeover when sufficient material is available at the counter electrode to balance the consumption of analyte at the working electrode; means for switching off the applied potential at time $t_{switch}$, and determining a time, $t_{mob}$, wherein $t_{mob}$ is the time after the applied potential is switched off, that it takes for the potential between the electrodes to decay to a pre-determined value, and means for calculating an expected value of $t_{peak}$, $t'_{peak}$, where $t'_{peak}$ is a function of $t_{mob}$, comparing the absolute value of $t_{peak}-t'_{peak}$ to a predetermined threshold value, and generating an error message if the absolute value of $t_{peak}-t'_{peak}$ is greater than the threshold value comprise circuits, such as on a circuit board associated with a programmed microprocessor that interacts with the circuits to provide the desired switching between amperometric and potentiometric modes and to monitor current and voltage as described, and storage components such as flash memory, EEPROMS or battery backed RAM. Apparatus suitable for switching between an amperometric mode of operation in which current is measured and a potentiometric mode of operation in which a potential difference between the electrodes is measured are described in commonly assigned U.S. Provisional Applications Nos. 60/521,592, filed May 30, 2004, and 60/594,285 filed Mar. 25, 2005, and U.S. patent application Ser. No. 10/907,790, filed Apr. 15, 2005, which are incorporated herein by reference.

Figure 8:
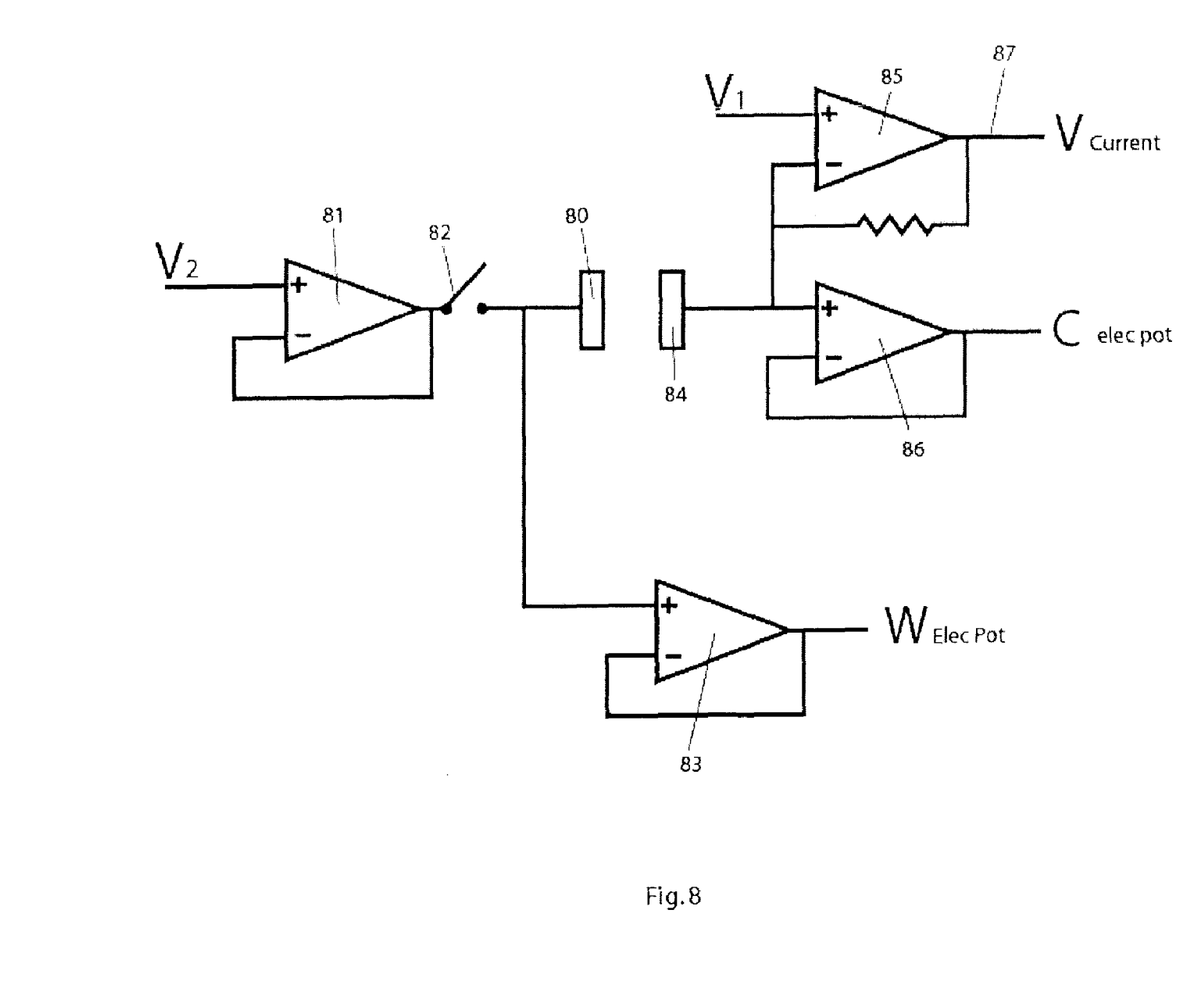
FIG. 8 shows a circuit diagram for switching between amperometric and potentiometric modes.

FIG. 8 shows an electrical schematic of a circuit useful as circuit 55 in FIG. 5. It will be appreciated, however, that other components can also be used, which achieve the same results in terms of applying and switching the voltage. Working electrode 80 is connected to op amp 81 via a connector containing switch 82, and to op amp 83. Counter electrode 84 is connected to op amps 85 and 86. Op amps 83, 85 and 86 are high impedance input amplifiers. When operating in amperometric mode to determine an analyte, a voltage $V_2$ is applied to op amp 81, and a voltage $V_1$ is applied to op amp 85, $V_2$ being greater than $V_1$. The resulting potential difference between the electrodes results in the generation of a current that is related to the amount of analyte, and this current can be monitored at output 87 and converted to an indication of the presence or amount of analyte. When switch 82 is opened to create an open circuit and stop application of the potential difference, current flow ceases, and the output of amplifier 86 assumes the potential of the counter electrode, while the output of amplifier 83 assumes the potential of the working electrode 80. The difference between the output from op amp 83 and op amp 86 indicates the decay in chemical potential and is processed in accordance with the methods described above to create an indication of partial fill.

Figure 9:
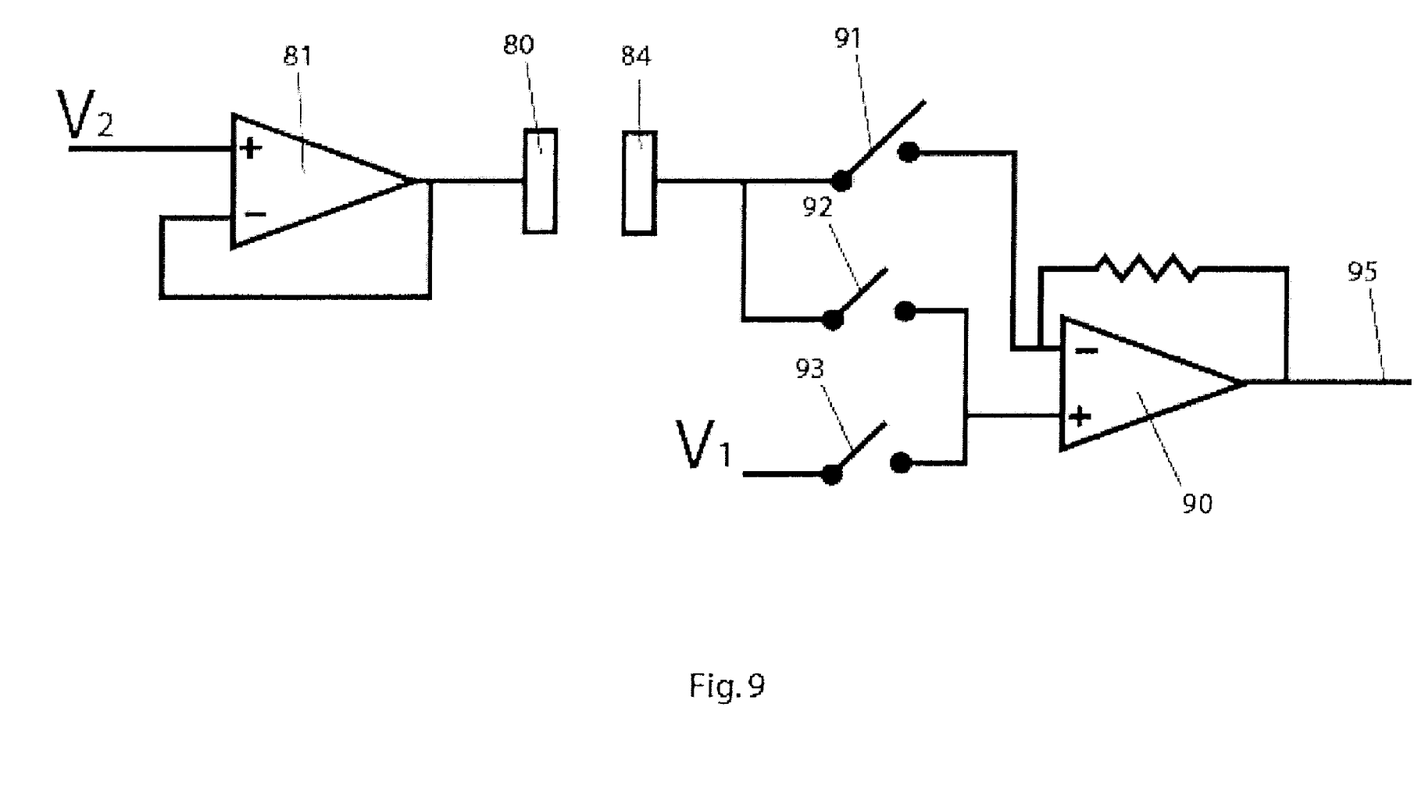
FIG. 9 shows a circuit diagram for switching between amperometric and potentiometric modes.

FIG. 9 shows an alternative version of this circuit using only two op amps and an increased number of switches. Working electrode 80 is connected to op amp 81 which received input voltage $V_2$. Counter electrode 84 is connected to high input impedance op amp 90 via one of two switched paths. Input voltage $V_1$ is connected to the circuit via a third switched path. When switch 91 and 93 are closed, and switch 92 is open, the circuit functions in amperometric mode, and the output at 95 reflects current flow at the electrodes. When switch 92 is closed, and switches 91 and 93 are open, the circuit operates in potentiometric mode and the output at 95 assumes the potential of the counter electrode (similar to amplifier 86 in FIG. 8). Thus, the output at 95 indirectly reflects the difference in potential between the electrodes. The actual difference in potential between the electrodes is the difference between the output at 95, and the output of op amp 81 (at 80, the working electrode).

VI. Measurement System

In actual use, the meter described above is combined with an electrochemical test strip for the determination of a particular analyte, such as glucose. This combination, referred to as a measurement system, forms a further aspect of the present invention.

What is claimed is:

1. A method for determination of an analyte in a sample comprising the steps of:
   (a) introducing the sample to an electrochemical test strip having working and counter electrodes;
   (b) applying a potential difference, $V_{app}$, between the electrodes of the test strip and observing a current signal sufficient to provide a determination of analyte in the sample;
   (c) determining a time $t_{peak}$, said time occurring at a maximum in the current at the point of changeover when sufficient material is available at the counter electrode to balance the consumption of analyte at the working electrode;
   (d) switching off the applied potential at time $t_{switch}$
   (e) determining a time, $t_{mob}$, wherein $t_{mob}$ is the time after the applied potential is switched off, that it takes for the potential between the electrodes to decay to a predetermined value,
   (f) calculating an expected value of $t_{peak}$, $t'_{peak}$, where $t'_{peak}$ is a function of $t_{mob}$, and
   (g) comparing the absolute value of $t_{peak}-t'_{peak}$ to a predetermined threshold value, rejecting the test if the absolute value of $t_{peak}-t'_{peak}$ is greater than the threshold value.

2. The method of claim 1, wherein $t'_{peak}$ is given by the equation:

$$t'_{peak}=[k_1 \times t_{mob} \times \text{CottrellSlope}^m]+[k_2 \times t_{mob}^n]+[k_3 \times t_{mob}^n \times \text{CottrellSlope}^m]+k_4$$

where $k_1$-$k_4$ are empirically determined constants, and the CottrellSlope is the square root of the slope of $1/I^2$ versus t in the Cottrell decay region of the current curve, and n and m are experimental positive or negative integer or fractional numbers.

3. The method of claim 2, wherein n is ½ and m is −1.

4. A meter for receiving an electrochemical test strip having working and counter electrodes and providing a determination of an analyte in a sample applied to the electrochemical test strip when received in the meter, said meter comprising
   (a) a housing having a slot for receiving an electrochemical test strip;
   (b) communications means for receiving input from and communicating a result to a user; and
   (c) means for applying a potential and to determine analyte concentration from an observed current,
   (d) means determining a time $t_{peak}$, said time occurring at a maximum in the current at the point of changeover when sufficient material is available at the counter electrode to balance the consumption of analyte at the working electrode;
   (e) means for switching off the applied potential at time $t_{switch}$, and determining a time, $t_{mob}$, wherein $t_{mob}$ is the time after the applied potential is switched off, that it takes for the potential between the electrodes to decay to a pre-determined value,
   (f) means for calculating an expected value of $t_{peak}$, $t'_{peak}$, where $t'_{peak}$ is a function of $t_{mob}$, comparing the absolute value of $t_{peak}-t'_{peak}$ to a predetermined threshold value, and generating an error message if the absolute value of $t_{peak}-t'_{peak}$ is greater than the threshold value.

5. The meter of claim 4, wherein $t'_{peak}$ is given by the equation:

$$t'_{peak}=[k_1 \times t_{mob} \times \text{CottrellSlope}^m]+[k_2 \times t_{mob}^n]+[k_3 \times t_{mob}^n \times \text{CottrellSlope}^m]+k_4$$

where $k_1$-$k_4$ are empirically determined constants, and the CottrellSlope is the square root of the slope of $1/I^2$ versus t in the Cottrell decay region of the current curve, and n and m are experimental positive or negative integer or fractional numbers.

6. The meter of claim 5, wherein n is ½ and m is −1.

7. A measurement system comprising a meter in accordance with claim 4 and an electrochemical test strip received within the housing.

8. The measurement system of claim 7, wherein the electrochemical test strip is for measurement of glucose.

9. The measurement system of claim 8, wherein $t'_{peak}$ is given by the equation:

$$t'_{peak}=[k_1 \times t_{mob} \times \text{CottrellSlope}^m]+[k_2 \times t_{mob}^n]+[k_3 \times t_{mob}^n \times \text{CottrellSlope}^m]+k_4$$

where $k_1$-$k_4$ are empirically determined constants, and the CottrellSlope is the square root of the slope of $1/I^2$ versus t in the Cottrell decay region of the current curve, and n and m are experimental positive or negative integer or fractional numbers.

10. The measurement system of claim 9, wherein n is ½ and m is −1.

11. The measurement system of claim 7, wherein $t'_{peak}$ is given by the equation:

$$t'_{peak}=[k_1 \times t_{mob} \times \text{CottrellSlope}^m]+[k_2 \times t_{mob}^n]+[k_3 \times t_{mob}^n \times \text{CottrellSlope}^m]+k_4$$

where $k_1$-$k_4$ are empirically determined constants, and the CottrellSlope is the square root of the slope of $1/I^2$ versus t in the Cottrell decay region of the current curve, and n and m are experimental positive or negative integer or fractional numbers.

12. The measurement system of claim 11, wherein n is ½ and m is −1.

* * * * *